(12) United States Patent
Otsuka et al.

(10) Patent No.: US 10,270,101 B2
(45) Date of Patent: Apr. 23, 2019

(54) ELECTRODE ACTIVE MATERIAL FOR POWER STORAGE DEVICE, AND POWER STORAGE DEVICE

(71) Applicant: Panasonic Corporation, Osaka (JP)

(72) Inventors: Yu Otsuka, Osaka (JP); Nobuhiko Hojo, Osaka (JP); Jun-ichi Yoshida, Osaka (JP); Toshiki Nokami, Tottori (JP); Akihiro Shimizu, Kyoto (JP)

(73) Assignee: Panasonic Corporation, Osaka (JP)

( * ) Notice: Subject to any disclaimer, the term of this patent is extended or adjusted under 35 U.S.C. 154(b) by 552 days.

(21) Appl. No.: 14/439,972

(22) PCT Filed: Mar. 11, 2014

(86) PCT No.: PCT/JP2014/001374
§ 371 (c)(1),
(2) Date: Apr. 30, 2015

(87) PCT Pub. No.: WO2014/141696
PCT Pub. Date: Sep. 18, 2014

(65) Prior Publication Data
US 2015/0295244 A1 Oct. 15, 2015

(30) Foreign Application Priority Data

Mar. 11, 2013 (JP) .................. 2013-048052

(51) Int. Cl.
*H01M 4/60* (2006.01)
*C07D 241/44* (2006.01)
(Continued)

(52) U.S. Cl.
CPC ............ *H01M 4/60* (2013.01); *C07D 241/44* (2013.01); *C07D 471/04* (2013.01);
(Continued)

(58) Field of Classification Search
CPC .............................. H01G 11/30; H01G 11/32
See application file for complete search history.

(56) References Cited

U.S. PATENT DOCUMENTS 6,277,518 B1    8/2001   Naoi et al.
6,413,675 B1    7/2002   Harada et al.
(Continued)

FOREIGN PATENT DOCUMENTS

EP      0 911 893 A1    4/1999
JP      H11-185759 A    7/1999
(Continued)

OTHER PUBLICATIONS

Liang, Yanliang, et al. "Function-Oriented Design of Conjugated Carbonyl Compound Electrodes for High Energy Lithium Batteries." Chemical Science, The Royal Society of Chemistry, Jan. 15, 2013.*
(Continued)

*Primary Examiner* — Stephan J Essex
(74) *Attorney, Agent, or Firm* — McDermott Will & Emery LLP

(57) ABSTRACT

An electrolyte solution for a secondary lithium battery, the electrolyte solution including: a lithium salt, a non-aqueous organic solvent, and a phenanthroline-based compound having a polar substituent. The electrolyte solution enables production of a secondary lithium battery having a good high-temperature lifetime characteristics and good high-temperature preservation characteristics.

4 Claims, 3 Drawing Sheets

(51) Int. Cl.
*C07D 471/04* (2006.01)
*C07D 487/04* (2006.01)
*H01G 11/32* (2013.01)
*H01M 10/0525* (2010.01)
*H01G 11/30* (2013.01)
*H01M 4/137* (2010.01)
*H01G 11/48* (2013.01)
*H01M 10/052* (2010.01)

(52) U.S. Cl.
CPC ........... *C07D 487/04* (2013.01); *H01G 11/30* (2013.01); *H01G 11/32* (2013.01); *H01G 11/48* (2013.01); *H01M 4/137* (2013.01); *H01M 4/608* (2013.01); *H01M 10/0525* (2013.01); *H01M 10/052* (2013.01); *H01M 2220/20* (2013.01); *H01M 2220/30* (2013.01); *Y02E 60/13* (2013.01); *Y02T 10/7022* (2013.01)

(56) References Cited

U.S. PATENT DOCUMENTS

| | | |
|---|---|---|
| 6,743,877 B1 | 6/2004 | Armand et al. |
| 2003/0118877 A1 | 6/2003 | Armand et al. |
| 2004/0101741 A1* | 5/2004 | Minteer ............... C12N 11/08 429/401 |
| 2004/0202930 A1 | 10/2004 | Armand et al. |
| 2010/0047688 A1 | 2/2010 | Ohtsuka et al. |
| 2010/0181527 A1 | 7/2010 | Nesvadba et al. |
| 2010/0196758 A1 | 8/2010 | Hojo et al. |
| 2010/0237298 A1 | 9/2010 | Armand et al. |
| 2012/0100439 A1* | 4/2012 | Kang ................ H01M 10/0525 429/341 |
| 2012/0270141 A1* | 10/2012 | Koshino ................ B01J 31/183 429/492 |
| 2013/0004836 A1 | 1/2013 | Otsuka et al. |

FOREIGN PATENT DOCUMENTS

| | | |
|---|---|---|
| JP | 3039484 B2 | 5/2000 |
| JP | 3045750 B2 | 5/2000 |
| JP | 2001-512526 A | 8/2001 |
| JP | 3257516 B2 | 2/2002 |
| JP | 2007-305430 A | 11/2007 |
| JP | 2010-530602 A | 9/2010 |
| JP | 2011-146221 A | 7/2011 |
| JP | 2012-113841 A | 6/2012 |
| WO | 2009-118990 A1 | 10/2009 |
| WO | 2011-111401 A1 | 9/2011 |
| WO | 2012-121145 A1 | 9/2012 |

OTHER PUBLICATIONS

PCT/ISA/237 issued in PCT/JP2014/001374, dated Jun. 17, 2014, with partial English translation.
International Search Report issued in PCT/JP2014/001374, dated Jun. 17, 2014, with English translation.

\* cited by examiner

ELECTRODE ACTIVE MATERIAL FOR POWER STORAGE DEVICE, AND POWER STORAGE DEVICE

RELATED APPLICATIONS

This application is the U.S. National Phase under 35 U.S.C. § 371 of International Application No. PCT/JP2014/001374, filed on Mar. 11, 2014, which in turn claims the benefit of Japanese Application No. 2013-048052, filed on Mar. 11, 2013, the disclosures of which Applications are incorporated by reference herein.

TECHNICAL FIELD

The present invention relates to an electrode active material for an electricity storage device, and an electricity storage device using the electrode active material.

BACKGROUND ART

Recently, various mobile information terminals and mobile game devices such as tablet-type information terminals and smart phones have become widely used. A secondary battery that is chargeable/dischargeable repeatedly is used as a power source of such a mobile electronic device. In addition, secondary batteries having a much larger capacity than a battery for mobile electronic devices have been increasingly desired. For example, hybrid vehicles that use both of a conventional internal combustion engine and an electric driving force, and electric vehicles that use a motor instead of the internal combustion engine are about to become widely used for saving energy or decreasing the carbon dioxide emissions. In such a situation, secondary batteries having higher characteristics, namely, a larger output, a larger capacity, a longer cycle life and the like are now desired for various uses.

A secondary battery stores charges by use of a redox reaction. Therefore, a substance reversibly oxidized and reduced, namely, an electricity storage material that stores charges, significantly influences these characteristics of a secondary battery. Conventional secondary batteries use metal materials, carbon, inorganic compounds and the like as electricity storage materials. In the case of, for example, a lithium secondary battery, which is in a wide use today, a metal oxide such as lithium cobalt oxide or the like, graphite, or the like is used as a positive electrode active material and a negative electrode active material, which are electricity storage materials.

It has been examined to use an organic compound as an electricity storage material instead of the inorganic material described above. An organic compound allows molecular design to be made in a more diversified manner than an inorganic material. Therefore, an active material formed of an organic compound is considered to have a variety of characteristics by molecular design. In addition, an organic compound is more lightweight than a metal material. Therefore, a secondary battery produced by use of an electricity storage material formed of an organic compound is considered to be lightweight.

For example, Patent Documents 1, 2 and 3 each disclose a secondary battery using a quinone-based compound as an electrode active material.

CITATION LIST

Patent Literature

Patent Document 1: Japanese Patent No. 3045750
Patent Document 2: Japanese Patent No. 3039484
Patent Document 3: Japanese Patent No. 3257516

SUMMARY OF INVENTION

Technical Problem

The secondary batteries disclosed in Patent Documents 1, 2 and 3 each have a discharge voltage that is lower than the discharge voltage of a conventional electricity storage device using an inorganic material such as lithium cobalt oxide or the like (3 to 4 V). In such a situation, an electric active material, for an electricity storage device, which contains an organic compound and can realize a higher discharge voltage has been desired.

A non-limiting illustrative embodiment according to the present invention provides an electric active material, for an electricity storage device, which contains an organic compound and can realize a higher discharge voltage, and an electricity storage device using such an electric active material.

Solution to Problem

An electrode active material for an electricity storage device in an embodiment according to the present invention includes a heteroaromatic compound including two or more carbonyl groups and containing two or more nitrogen atoms, wherein carbon atoms of the two or more carbonyl groups and the two or more nitrogen atoms are included in a framework of the heteroaromatic compound.

Advantageous Effects of Invention

An electrode active material for an electricity storage device according to an embodiment of the present invention includes a heteroaromatic compound including two or more carbonyl groups and containing two or more nitrogen atoms. Such a heteroaromatic compound has a high redox potential. Therefore, the electrode active material in an embodiment of the present invention can realize an electricity storage device having a high discharge voltage.

DESCRIPTION OF EMBODIMENTS

Figure 1:
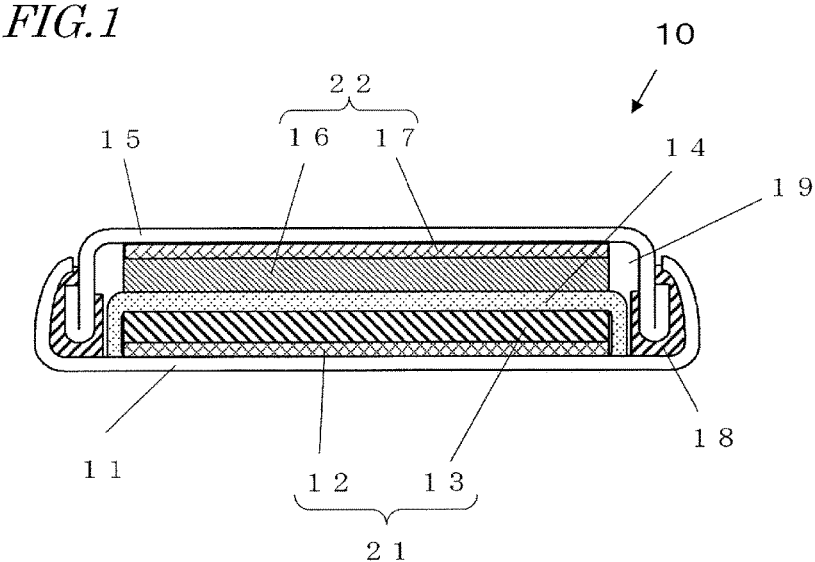
FIG. 1 is a cross-sectional view showing an example of electricity storage device in an embodiment according to the present invention.

The present inventors studied, in detail, cyclic compounds including two or more ketone groups as organic compounds acting as an electrode active material, and as a result, have found that various cyclic ketone compounds disclosed in WO2009/118990 and WO2011/111401 are usable as an electrode active material for an electricity storage device. The present inventors have also found that the compounds disclosed in WO2009/118990 and WO2011/111401 have a redox voltage of higher than or equal to about 2.8 V (on the basis of Li/Li$^+$) and can realize an electricity storage device having a higher discharge voltage than that of an electricity storage device including any conventional organic compound reported as an electrode active material for an electricity storage device, especially an electricity storage device including a quinone-based compound.

The present inventors further examined a structure for raising the redox potential, and have found that a heteroaromatic compound that contains carbon of a carbonyl group in a framework and further contains nitrogen has a high redox potential. An embodiment according to the present invention is as follows.

An electrode active material for an electricity storage device in an embodiment according to the present invention includes a heteroaromatic compound including two or more carbonyl groups and containing two or more nitrogen atoms, and carbon atoms of the two or more carbonyl groups and the two or more nitrogen atoms are included in a framework of the heteroaromatic compound.

The two or more nitrogen atoms may be respectively bonded to the carbon atoms to which the two or more carbonyl groups are respectively bonded.

The heteroaromatic compound may include n pairs (n is an integer of one or greater) of carbonyl groups, and two carbonyl groups of each of the n pairs may be located at ortho positions of an aromatic ring of the heteroaromatic compound.

The heteroaromatic compound may include three or more aromatic rings.

The heteroaromatic compound may be represented by the following general formula (1), (1'), (2), (3) or (11), and in the general formulas (1), (1'), (2), (3) and (11) $R_1$ through $R_6$, $R'_1$ through $R'_6$, $R_{10}$, $R_{11}$, $R_{21}$ through $R_{24}$, $R_{31}$ through $R_{34}$ may be independently a hydrogen atom, a halogen atom, a phenyl group which may include a substituent, a complex ring group which may include a substituent, or a hydrocarbon group of a carbon number of 1 through 4 which may include a substituent.

[Chemical formula 1]

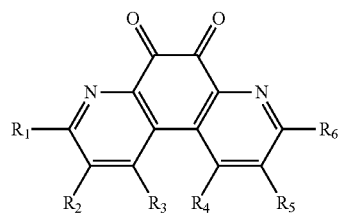

(1)

[Chemical formula 2]

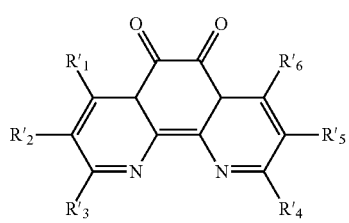

(1')

[Chemical formula 3]

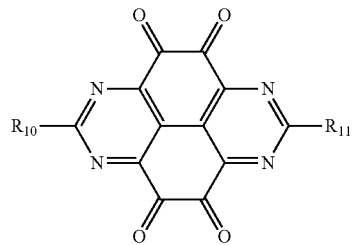

(2)

[Chemical formula 4]

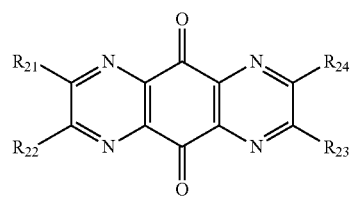

(3)

[Chemical formula 5]

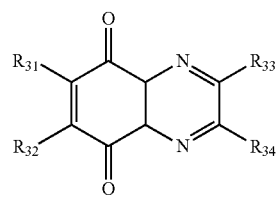

(11)

The heteroaromatic compound may be represented by the following chemical formula (4), (4'), (5), (6) or (12).

[Chemical formula 6]

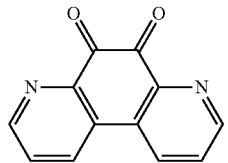

(4)

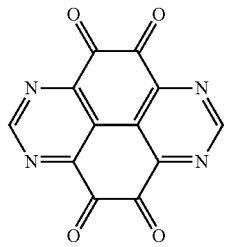

(5)

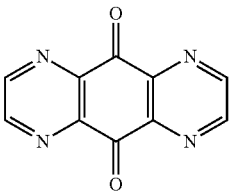

(6)

-continued

[Chemical formula 7]

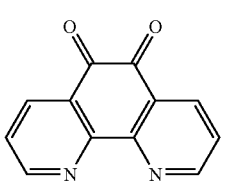
(4')

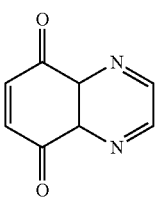
(12)

The heteroaromatic compound may be a polymeric compound.

At least one of the two or more nitrogen atoms of the heteroaromatic compound may be a quaternary ammonium ion.

The heteroaromatic compound may be represented by the following chemical formula (14).

[Chemical formula 8]

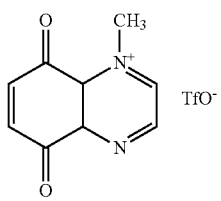
(14)

An electricity storage device in another embodiment according to the present invention includes a positive electrode, a negative electrode, and an electrolyte; and at least one selected from the positive electrode and the negative electrode includes an electrode active material for an electricity storage device described in any one of the above as an electrode active material.

Hereinafter, embodiments according to the present invention will be described in detail.

First Embodiment

An electrode active material for an electricity storage device in an embodiment according to the present invention includes a heteroaromatic compound including two or more carbonyl groups. Carbon and nitrogen of the carbonyl groups are contained in a framework of the heteroaromatic compound, namely, a heteroaromatic ring.

By substituting carbon atoms of the aromatic ring with nitrogen atoms, the state of electrons of the aromatic ring is changed and the potential at which a redox reaction of oxygen of the carbonyl groups occurs is raised.

Especially, a heteroaromatic compound in which nitrogen atoms are bonded to carbon atoms to which the carbonyl groups are respectively bonded has a still higher redox potential. An estimated reason for this will be described regarding 4,7-phenanthroline-5,6-dione as an example in comparison with phenanthrene-9,10-dione, which does not contain nitrogen.

As shown by reaction formula (I) below, phenanthrene-9,10-dione, which does not contain nitrogen, causes a 2-electron reduction reaction. It is considered that in phenanthrene-9,10-dione, as a result of the 2-electron reduction reaction, electrons are mainly delocalized to two oxygen atoms of the ketone group and two lithium ions are coordinated mainly to the oxygen atoms.

[Chemical formula 9]

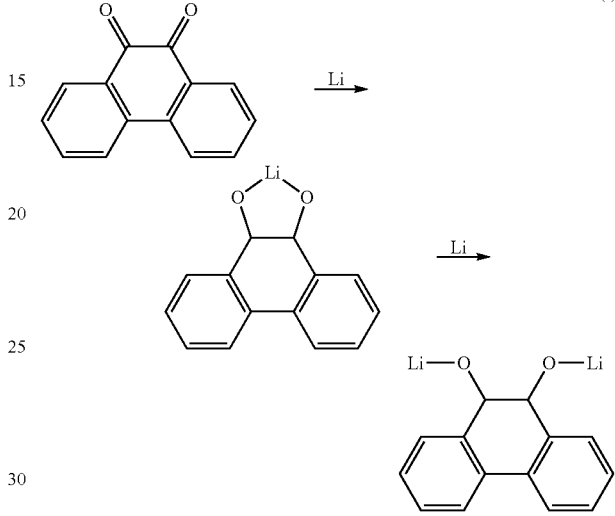
(I)

By contrast, as shown by reaction formula (II) below, it is considered that in 4,7-phenanthroline-5,6-dione, which contains nitrogen, as a result of the 2-electron reduction, electrons are delocalized to nitrogen atoms of the heteroaromatic ring as well as to the two oxygen atoms of the ketone group, and two lithium ions may be coordinated to the oxygen atoms and the nitrogen atoms. Based on the energy level calculated from the first principles calculation, it is estimated that the reduction reaction represented by reaction formula (II) occurs at a higher potential because nitrogen atoms are bonded to carbon atoms to which the carbonyl groups are bonded, namely, each carbonyl group and the corresponding nitrogen atom are located while having the carbon atom therebetween. Herein, the two nitrogen atoms are each included in a tertiary amine including a double bond and a single bond.

[Chemical formula 10]

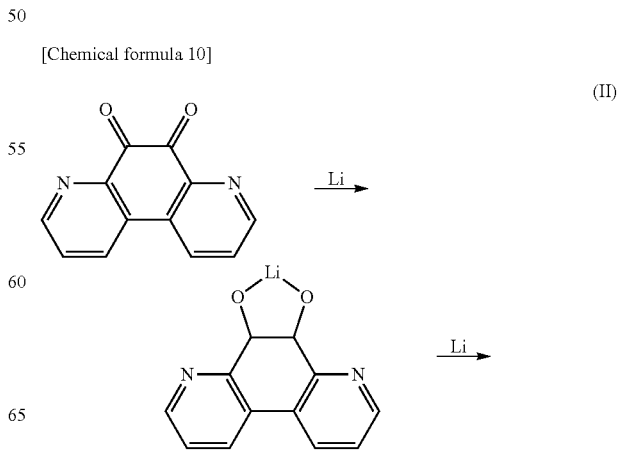
(II)

-continued

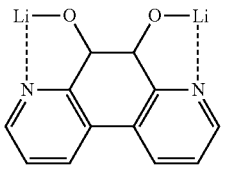

The two carbonyl groups are located at ortho positions, and therefore the electrons may be delocalized to the two oxygen atoms as described above. For this reason, the compound in the reduced state is stabilized. When 4,7-phenanthroline-5,6-dione in the reduced state is to be oxidized, the electrons are desorbed relatively easily because of the localization thereof. Therefore, 4,7-phenanthroline-5,6-dione can cause a reversible redox reaction smoothly. As described in examples later, a heteroaromatic compound including two carbonyl groups in this embodiment can be oxidized/reduced at a voltage of higher than or equal to 3 V on the basis of the redox potential of lithium. Therefore, such a heteroaromatic compound can realize an electricity storage device having a higher discharge voltage than the conventional organic compound.

As described above, a heteroaromatic compound included in an electrode active material for the electricity storage device in this embodiment includes two carbonyl groups and contains nitrogen in the framework, and therefore the redox potential of oxygen of the carbonyl groups is raised. In addition, since two or more nitrogen atoms are bonded to carbon atoms to which the two or more carbonyl groups are respectively bonded, the redox potential of oxygen of the carbonyl groups is further raised.

The heteroaromatic compound may include two or more carbonyl groups. Specifically, the heteroaromatic compound includes n pairs (n is an integer of one or greater) of carbonyl groups, and two carbonyl groups of each of the n pairs may be located at ortho positions of the aromatic ring of the heteroaromatic compound. In this case, the two carbonyl groups of each pair can cause a 2-electron redox reaction, and the reduced state is stabilized by the delocalization of the electrons as described above.

The heteroaromatic compound may include three or more aromatic rings. In this case, a stable heteroaromatic framework can be provided even with a structure in which two carbonyl groups are located at ortho positions and nitrogen atoms are located so as to be bonded to carbon atoms to which carbon atoms of the carbonyl groups are respectively bonded.

More specifically, the heteroaromatic compound included in the electrode active material for an electricity storage device in this embodiment may have a structure represented by the following general formula (1), (1'), (2), (3) or (11).

[Chemical formula 11]

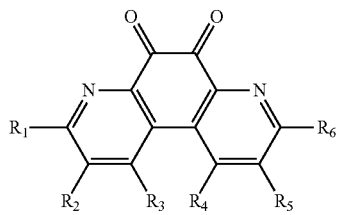

(1)

[Chemical formula 12]

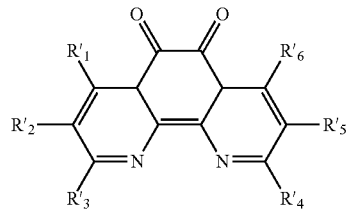

(1')

[Chemical formula 13]

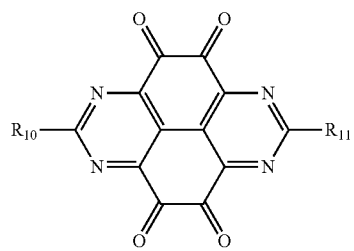

(2)

[Chemical formula 14]

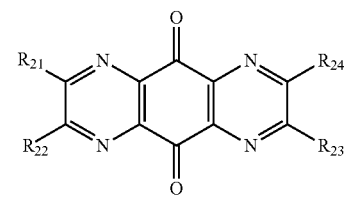

(3)

[Chemical formula 15]

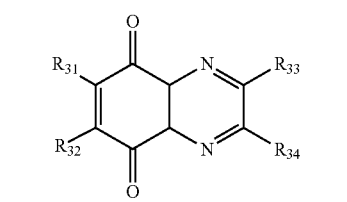

(11)

In general formulas (1), (1'), (2), (3) and (11), $R_1$ through $R_6$, $R'_1$ through $R'_6$, $R_{10}$, $R_{11}$, $R_{21}$ through $R_{24}$, and $R_{31}$ through $R_{34}$ are independently a hydrogen atom, a halogen atom, a phenyl group which may include a substituent, a complex ring group which may include a substituent, or a hydrocarbon group of a carbon number of 1 through 4 which may include a substituent. In this specification, the expression "may include a substituent" means that at least one hydrogen atom may be substituted with an appropriate group.

The substituent in the phenyl group which may include a substituent may be, for example, a group including at least one selected from the group consisting of a fluorine atom, a nitrogen atom, an oxygen atom, a sulfur atom, and a silicon atom. Examples of the group including a fluoride atom include fluorine atom, fluoroalkyl group, fluoroalkenyl group, and fluoroalkoxy group. Examples of the group including a nitrogen atom include nitro group, amino group, amide group, imino group, and cyano group. Example of the group including an oxygen atom include hydroxy group, oxo group, and carboxy group. Examples of the group including a sulfur atom include alkylthio group, sulfo group, sulfino group, sulfeno group, and mercapto group. Examples of the group including a silicon atom include silyl group.

The complex ring group may have a 5-member structure or a 6-member structure. Specific examples of the complex ring group include thiophene, furan, pyrrole, and azole. Cyclic ether, lactone, cyclic imine, lactam and the like may also form a complex ring group. A polycyclic complex ring group such as purine or the like, or a complex ring group having three elements (C, N, S) in a ring such as thiazole may be adopted. The substituent in the complex ring group which may include a substituent may be, for example, a group including at least one selected from the group consisting of a fluorine atom, a nitrogen atom, an oxygen atom, a sulfur atom, and a silicon atom. Examples of the group including a fluoride atom include fluorine atom, fluoroalkyl group, fluoroalkenyl group, and fluoroalkoxy group. Examples of the group including a nitrogen atom include nitro group, amino group, amide group, imino group, and cyano group. Examples of the group including an oxygen atom include hydroxy group, oxo group, and carboxyl group. Examples of the group including a sulfur atom include alkylthio group, sulfo group, sulfino group, sulfeno group, and mercapto group. Examples of the group including a silicon atom include silyl group.

The hydrocarbon group of a carbon number of 1 through 4 may be saturated, may have an unsaturated bond, or may form a ring. Examples of an alkyl group having a carbon number of 1 through 4 include straight-chain and branched-chain alkyl groups having a carbon number of 1 through 4, such as methyl group, ethyl group, propyl group, isopropyl group, butyl group, isobutyl group, sec-butyl group, tert-butyl group and the like. Examples of an alkenyl group having a carbon number of 2 through 4 include straight-chain and branched-chain alkenyl groups having 1 through 3 double bonds, such as allyl group, 1-propenyl group, 1-methyl-1-propenyl group, 2-methyl-1-propenyl group, 2-propenyl group, 2-butenyl group, 1-butenyl group, 3-butenyl group and the like.

The substituent in the hydrocarbon group of a carbon number of 1 through 4 which may include a substituent may be, for example, a group including at least one selected from the group consisting of a fluorine atom, a nitrogen atom, an oxygen atom, a sulfur atom, and a silicon atom. Examples of the group including a fluoride atom include fluorine atom, fluoroalkyl group, fluoroalkenyl group, and fluoroalkoxy group. Examples of the group including a nitrogen atom include nitro group, amino group, amide group, imino group, and cyano group. Examples of the group including an oxygen atom include hydroxy group, oxo group, and carboxyl group. Examples of the group including a sulfur atom include alkylthio group, sulfo group, sulfino group, sulfeno group, and mercapto group. Examples of the group including a silicon atom include silyl group.

In the heteroaromatic compound represented by general formula (1), $R_1$ through $R_6$ may all be hydrogen atoms. In this case, the heteroaromatic compound represented by general formula (1) is 4,7-phenanthroline-5,6-dione represented by the following formula (4) (hereinafter, may be referred to as "compound (4)").

[Chemical formula 16]

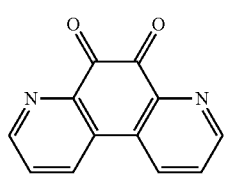

(4)

Alternatively, in the heteroaromatic compound represented by general formula (1), four selected from $R_1$ through $R_6$ may be hydrogen atoms, and the other two may be independently a halogen atom, a phenyl group which may include a substituent, a complex ring group which may include a substituent, or a hydrocarbon group of a carbon number of 1 through 4 which may include any of the substituents described above. For example, the two other than the four selected from $R_1$ through $R_6$ may be $R_2$ and $R_5$.

In the heteroaromatic compound represented by general formula (1'), $R'_1$ through $R'_6$ may all be hydrogen atoms. In this case, the heteroaromatic compound represented by general formula (1') is 1,10-phenanthroline-5,6-dione represented by the following formula (4') (hereinafter, may be referred to as "compound (4')").

[Chemical formula 17]

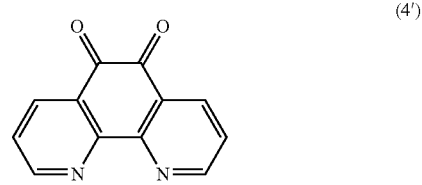

(4')

In the heteroaromatic compound represented by general formula (2), $R_{10}$ and $R_{12}$ may both be hydrogen atoms. In this case, the heteroaromatic compound represented by general formula (2) is 1,3,6,8-tetraazapyrene-4,5,9,10-tetraone represented by the following formula (5) (hereinafter, may be referred to as "compound (5)").

[Chemical formula 18]

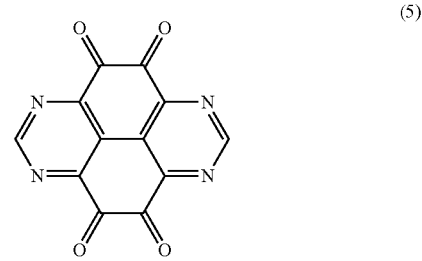

(5)

In the heteroaromatic compound represented by general formula (3), $R_{21}$ through $R_{24}$ may all be hydrogen atoms. In this case, the heteroaromatic compound represented by general formula (3) is pyrazino[2,3-g]quinoxaline-5,10-dione represented by the following formula (6) (hereinafter, may be referred to as "compound (6)").

[Chemical formula 19]

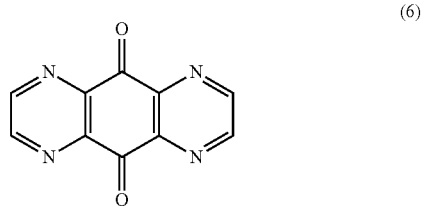

(6)

In the heteroaromatic compound represented by general formula (4), $R_{31}$ through $R_{34}$ may all be hydrogen atoms. In this case, the heteroaromatic compound represented by general formula (4) is quinoxaline-5,8-dione represented by the following formula (12) (hereinafter, may be referred to as "compound (12)").

[Chemical formula 20]

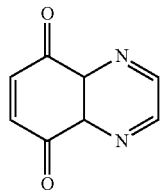

(12)

In the heteroaromatic compound represented by general formula (1'), $R'_1$, $R'_2$, $R'_5$ and $R'_6$ may be hydrogen atoms, and $R'_3$ and $R'_4$ may be chlorine atoms. In this case, the heteroaromatic compound represented by general formula (1') is 2,9-dichloro-1,10-phenanthroline-5,6-dione represented by the following formula (13) (hereinafter, may be referred to as "compound (13)").

[Chemical formula 21]

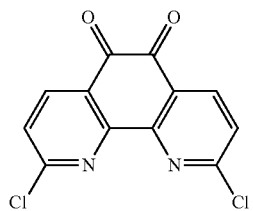

(13)

In the case where an electrode active material in this embodiment is used for an electricity storage device, it is preferable that the electrode active material in this embodiment is not easily dissolved in the electrolyte. Specifically, in the case where a non-aqueous electrolytic solution containing support salt dissolved therein is used as the electrolyte, it is preferable that the electrode active material in this embodiment is not easily dissolved in a non-aqueous solvent that forms the non-aqueous electrolytic solution. The materials of $R_1$ through $R_6$, $R'_1$ through $R'_6$, $R_{10}$, $R_{11}$, $R_{21}$ through $R_{24}$, and $R_{31}$ through $R_{34}$ in general formulas (1), (1'), (2), (3) and (11) may be selected based on the capability of decreasing the solubility of the electrode active material in the non-aqueous solvent to be used.

In order to have a lower solubility in the electrolyte, the electrode active material may be formed of a polymeric compound containing a heteroaromatic compound including the two or more carbonyl groups described above instead of, or in addition to, the substituents to be introduced into $R_1$ through $R_6$, $R'_1$ through $R'_6$, $R_{10}$, $R_{11}$, $R_{21}$ through $R_{24}$, and $R_{31}$ through $R_{34}$ in general formulas (1), (1'), (2), (3) and (11) described above. Specifically, the electrode active material for an electricity storage device in this embodiment may contain a polymeric compound including, in a main chain or a side chain, a heteroaromatic compound including the above-described two or more carbonyl groups and also containing two or more nitrogen atoms. More specifically, the electrode active material in this embodiment may be a polymeric compound including a heteroaromatic compound represented by general formula (1), (1'), (2), (3) or (11) as a repeat unit. In general, a polymeric compound has a lower solubility than that of a monomer that forms a repeat unit. Therefore, it is effective to polymerize a heteroaromatic compound represented by general formulas (1), (1'), (2), (3) or (11) in order to decrease the solubility of the electrode active material in any of various solvents.

For example, either two of $R_1$ through $R_6$ in the structure represented by general formula (1), either two of $R'_1$ through $R'_6$ in the structure represented by general formula (1'), $R_{10}$ and $R_{11}$ in the structure represented by general formula (2), either two of $R_{21}$ through $R_{24}$ in the structure represented by general formula (3), or either two of $R_{31}$ through $R_{34}$ in the structure represented by general formula (11) may be bonding hands, and the heteroaromatic ring of the structure represented by general formula (1), (1'), (2), (3) or (11) may form a main chain of the polymer compound. In this case, the either two of $R_1$ through $R_6$, the either two of $R'_1$ through $R'_6$, $R_{10}$ and $R_{11}$, the either two of $R_{21}$ through $R_{24}$ or the either two of $R_{31}$ through $R_{34}$ may be bonded with bonding hands of adjacent structural units directly or via any of the above-described substituents or the like. A polymeric compound including the structure represented by general formula (1), (1'), (2), (3) or (11) in a main chain can decrease the number of carbon atoms that do not contribute to electricity storage. Therefore, an electricity storage device having a higher energy density can be realized.

Alternatively, either one of $R_1$ through $R_6$ in the structure represented by general formula (1), either one of $R'_1$ through $R'_6$ in the structure represented by general formula (1'), either one of $R_{10}$ and $R_{11}$ in the structure represented by general formula (2), either one of $R_{21}$ through $R_{24}$ in the structure represented by general formula (3), or either one of $R_{31}$ through $R_{34}$ in the structure represented by general formula (11) may be a bonding hand, and may be bonded with a main chain of the polymeric compound directly or via a substituent or the like. A polymeric compound including the structure represented by general formula (1), (1'), (2), (3) or (11) in a side chain can optionally select the structure or the like of the main chain. Therefore, the synthesis of such a polymeric compound is easy, or the freedom of design of such a polymeric compound is raised.

In the electrode active material in this embodiment, the nitrogen atoms are contained in the heteroaromatic ring each as a part of the tertiary amine. Alternatively, the nitrogen atoms may be contained in the heteroaromatic ring each as a quaternary ammonium ion. In this case, the nitrogen atoms may each be bonded with a substituent R" in addition to the single bond and the double bond that form the heteroaromatic ring. R" is a hydrogen atom, a halogen atom, a phenyl group which may include a substituent, a complex ring group which may include a substituent, or a hydrocarbon group of a carbon number of 1 through 4 which may include a substituent. The details of these substituents are as described above.

In this case, the electrode active material in this embodiment contains anion. Examples of the anion include halide anion, perchloric acid anion, trifluoromethansulfonic acid anion, tetraborofluoride anion, trifluorophosphorus hexafluoride anion, trifluoromethanesulfonic acid anion, bis(trifluoromethanesulfonyl)imide anion, and bis(perfluoroethylsulfonyl)imide anion.

For example, in the heteroaromatic compound represented by general formula (4), $R_{31}$ through $R_{34}$ may all be hydrogen atoms, and the nitrogen atom at position 1 may be a quaternary ammonium ion bonded with a methyl group. In this case, the heteroaromatic compound represented by general formula (4) is a salt, and is 1-methyl-5,8-dioxo-5,8-dihydroquinoxalinium trifluoromethanesulfonate represented by the following formula (14) (hereinafter, may be referred to as "compound (14)").

[Chemical formula 22]

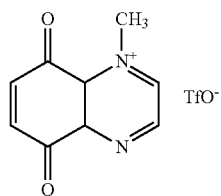

(14)

The electrode active material in this embodiment may be a polymeric compound including a salt of a heteroaromatic compound in a repeat unit. In this case, the nitrogen atoms may each have a single bond and a double bond that form a heteroaromatic ring and may be bonded with a substituent R", and the substituent R" may be bonded to the main chain of the polymeric compound directly or via a substituent.

For example, in the heteroaromatic compound represented by general formula (1), $R_1$ through $R_6$ may all be hydrogen atoms, and the nitrogen atom at position 4 may be bonded with the main chain of the polymeric compound via a benzyl group. In this case, the heteroaromatic compound represented by general formula (1) is a polymeric compound, and is poly[5,6-dioxo-4-(4-vinylbenzyl)-5,6-dihydro-4,7-phenanthroline-4-ium chloride] represented by the following formula (15) (hereinafter, may be referred to as "compound (15)").

[Chemical formula 23]

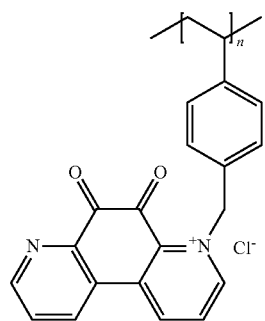

(15)

An electrode active material for an electricity storage device in this embodiment includes a heteroaromatic compound having the above-described structure, and therefore can realize an electricity storage device having a high discharge voltage. Since the electrode active material can be formed of an organic compound, an electricity storage device having a high energy density can be realized.

Second Embodiment

An electricity storage device for an electricity storage device in an embodiment according to the present invention will be described. In this embodiment, a coin-shaped lithium ion secondary battery will be described as an electricity storage device. As shown in FIG. 1, a lithium ion secondary battery 10 includes a positive electrode 21, a negative electrode 22, a separator 14 located between the positive electrode 21 and the negative electrode 22, and an electrolyte 19. These elements are accommodated in a case 11 by use of a gasket 18 and a sealing plate 15. At least one of the positive electrode 21 and the negative electrode 22 contains an electrode active material in this embodiment. Namely, the electrode active material in this embodiment is usable for both of, or one of, the positive electrode 21 and the negative electrode 22. In the case where the electrode active material in this embodiment is used for either one of the positive electrode 21 and the negative electrode 22, a conventional electrode active material is usable for the other electrode.

The positive electrode 21 includes, for example, a positive electrode current collector 12 and a positive electrode active material layer 13 formed on the positive electrode current collector 12. The positive electrode active material layer 13 is located between the positive electrode current collector 12 and the separator 14 so as to be in contact with both of the positive electrode current collector 12 and the separator 14.

The positive electrode current collector 12 may be formed of, for example, a porous or non-porous sheet of a metal material such as aluminum, stainless steel, an aluminum alloy or the like. The sheet formed of the metal material may be, for example, a metal foil or a metal mesh body. A carbon material such as carbon or the like may be applied to a surface of the positive electrode current collector 12 in order to (i) decrease the electrode resistance, (ii) provide a catalytic effect and (iii) couple the positive electrode active material layer 13 and the positive electrode current collector 12 chemically or physically and thus strengthen the coupling of the positive electrode active material layer 13 and the positive electrode current collector 12.

The positive electrode active material layer 13 is provided on at least one surface of the positive electrode current collector 12. The positive electrode active material layer 13 contains a positive electrode active material and may contain a conductive additive, an ion conductive additive, a binder or the like when necessary.

The conductive additive and the ion conductive additive are used to decrease the electrode resistance. Examples of the conductive additive include carbon materials such as carbon black, graphite, acetylene black and the like; and conductive polymeric compounds such as polyaniline, polypyrrole, polythiophene and the like. Examples of the ion conductive additive include gel electrolytes such as polymethylmethacrylate and poly(methyl methacrylate) and the like; and solid electrolytes such as polyethyleneoxide and the like.

The positive electrode 21 may be produced as follows. A powdery positive electrode active material (e.g., nitrogen-containing orthoquinone compound), a powdery conductive additive and a powdery ion conductive additive are mixed, and the resultant mixture is formed into a sheet. The resultant sheet is put into pressure contact with a sheet-like or mesh current collector. Alternatively, the positive electrode 21 may be produced as follows. A positive electrode active material, a conductive additive, a binder and an organic solvent are mixed to prepare a slurry. The slurry is applied to the current collector, and then the organic solvent is removed. In this case, the positive electrode active material may be dissolved in an organic solvent, and then a conductive additive, a binder and any other material may be mixed therewith to form a slurry. The slurry may be used to produce the positive electrode 21.

The slurry may be prepared as follows. An electrode active material is dissolved in a non-protonic solvent, and the resultant solution is mixed with a conductive additive. Alternatively, an electrode active material may be dissolved in a mixture containing a non-protonic solvent and a conductive additive. The mixture may contain a binder. Materials usable as the binder will be described later. The conductive additive and the binder do not need to be dissolved in the non-protonic solvent. In the case where the mixture contains the binder, the order in which the materials are mixed is arbitrary. It is desirable that the electrode active material is dissolved in the non-protonic solvent and uniformly dispersed. In the case where the electrode active material is dissolved in the non-protonic solvent and then mixed with the conductive additive, the electrode active material in a molecular state covers a surface of the conductive additive. Therefore, in order to be uniformly dispersed, the electrode active material is desirably dissolved in the non-protonic solvent.

There is no specific limitation on the material used as the non-protonic solvent. A material that has high affinity with any of the above-described electrode active materials is preferable. Specific examples of the preferable materials include non-protonic solvents such as N-methylpyrrolidone (NMP), 1,3-dimethyl-2-imidazolidinone (DMI), tetrahydrofuran (THF), toluene, dimethylformamide (DMF), dimethylacetamide (DMAc), dimethylsulfoxide (DMSO), chloroform and the like. NMP, DMI and THF are more preferable.

The binder is used for, for example, improving the bindability of the materials of the electrode. Examples of the materials usable as the binder include polyvinylidenefluoride, vinylidene fluoride-hexafluoropropylene copolymer, vinylidene fluoride-tetrafluoroethylene copolymer, polytetrafluoroethylene, styrene-butadiene copolymeric rubber, polypropylene, polyethylene, polyimide and the like.

The negative electrode 22 includes, for example, a negative electrode current collector 17 and a negative electrode active material layer 16 formed on the negative electrode current collector 17. The negative electrode active material layer 16 is located between the negative electrode current collector 17 and the separator 14 so as to be in contact with both of the negative electrode current collector 17 and the separator 14.

The negative electrode current collector 17 may be formed of a porous or non-porous sheet of a metal material such as copper, nickel, a copper alloy, a nickel alloy or the like or any of the materials usable for the positive electrode current collector 12. A carbon material may be applied to a surface of the negative electrode current collector 17 in order to decrease the electrode resistance, to provide a catalytic effect and to strengthen the coupling of the negative electrode active material layer 16 and the negative electrode current collector 17.

The negative electrode active material layer 16 is provided on at least one surface of the negative electrode current collector 17. The negative electrode active material layer 16 contains a negative electrode active material and may contain a conductive additive, an ion conductive additive, a binder or the like when necessary. Specifically, the conductive additive, the ion conductive additive and the binder that are same as those contained in the positive electrode active material layer 17 are usable.

In the case where an electrode active material in the first embodiment is used for the positive electrode 21, a material having a capability of occluding and releasing lithium ions is usable as the negative electrode active material. Examples of the material having a capability of occluding and releasing lithium ions include the following: carbon materials such as carbon, graphite, amorphous carbon and the like; lithium metal; lithium compounds such as lithium-containing composite nitride, lithium-containing titanium oxide and the like; Si; Si compounds such as Si oxide, Si alloy and the like; Sn; and Sn compounds such as Sn oxide, Sn alloy and the like.

A lithium ion secondary battery having a discharge voltage of higher than or equal to 3 V can be realized by use of an electrode active material in the first embodiment as the positive electrode active material and a material having a capability of occluding and releasing lithium ions as described above. In this case, the battery 10 can be produced by use of an arbitrary non-aqueous electrolyte. The electrode active material in this embodiment does not contain lithium ions. Therefore, when the electrode active material in this embodiment is used as the positive electrode active material, the negative electrode active material needs to contain lithium ions. For example, in the case where a material that does not contain lithium ions such as a carbon material, Si, an Si compound, Sn, an Sn compound or the like is used as the negative electrode active material, the negative electrode active material layer 16 is formed on the negative electrode current collector 17 and then the step of causing the negative electrode active material layer 16 to occlude lithium ions is performed. Specifically, lithium is deposited on the negative electrode active material layer 16 by a known method such as vapor deposition, sputtering or the like, and lithium is diffused in the negative electrode active material layer 16. Thus, the negative electrode 22 having lithium occluded in advance is produced. In order to promote the diffusion of the deposited lithium in the negative electrode active material layer 16, the negative electrode 22 may be heat-treated. Alternatively, a lithium metal foil may be provided on the negative electrode active material layer 16 and heat-treated, so that lithium is occluded in the negative electrode 22.

In the case where an electrode active material in this embodiment is used for the negative electrode 22, the material usable as the positive electrode active material is a lithium-containing metal oxide such as $LiCoO_2$, $LiNiO_2$, $LiMn_2O_4$ or the like; activated carbon, an oxidizable and reducible organic compound or the like.

Examples of the oxidizable and reducible organic compound include organic compounds having π-conjugated electron cloud in a molecular which are represented by tetrathiafulvalene ring, and organic compounds having a stable radical in a molecular which are represented by nitroxy radical.

The separator 14 is formed of a material having a predetermined ion permeability, a predetermined mechanical strength and a predetermined insulating property, for example, a microporous sheet, a woven cloth or a non-woven cloth. The microporous sheet, the woven cloth and the non-woven cloth are usually formed of a resin material. It is preferable that the separator 14 is formed of polyolefin such as polyethylene, polypropylene or the like from the points of view of durability, shutdown function, and battery safety. The "shutdown function" refers to a function by which, when the amount of heat generation of the battery 10 is significantly increased, the through-hole is closed, thus ion permeation is suppressed, and the battery reaction is blocked.

The electrolyte may be, for example, a liquid electrolyte, a solid electrolyte, a gel electrolyte or the like. The liquid electrolyte contains a solvent and a support salt. The support salt may be a support salt that is commonly used for lithium ion batteries and non-aqueous electric double-layer capacitors. Specifically, support salts formed of the following cation and anion are usable. Examples of the cation include cations of alkaline metals such as lithium, sodium, potassium and the like; cations of alkaline earth metals such as magnesium and the like; and cations of quaternary ammoniums such as tetraethylammonium, 1,3-ethylmethylimidazolium and the like. These cations may be used independently or in a combination of two or more. Examples of the anion include halide anion, perchloric acid anion, trifluoromethansulfonic acid anion, tetraborofluoride anion, trifluorophosphorus hexafluoride anion, trifluoromethanesulfonic acid anion, bis(trifluoromethanesulfonyl)imide anion, and bis(perfluoroethylsulfonyl)imide anion. These anions may be used independently or in a combination of two or more. A preferable support salt is a lithium salt formed of lithium cation and any of the above-described anions.

In the case where the support salt is liquid, the support salt and a solvent may or may not be mixed together. In the case where the support salt is solid, it is preferable that a solution obtained by dissolving the support salt in an appropriate solvent is used as the electrolyte. The solvent may be a solvent commonly used in the field of lithium ion batteries and non-aqueous electric double-layer capacitors. Examples of the materials usable as the solvent include ethylene carbonate, propylene carbonate, dimethyl carbonate, diethyl carbonate, methylethyl carbonate, γ-butyl lactone, tetrahydrofuran, dioxorane, sulforane, dimethylformamide, and acetonitrile. These organic solvents may be used independently or in a combination of two or more.

Examples of the materials usable as the solid electrolyte include $Li_2S$—$SiS_2$-lithium compound (herein, the lithium compound is at least one selected from the group consisting of $Li_3PO_4$, LiI and $Li_4SiO_4$), $Li_2S$—$P_2O_5$, $Li_2S$—$B_2S_5$, $Li_2S$—$P_2S_5$—$GeS_2$, sodium/alumina ($Al_2O_3$), amorphous polyether having a low phase transition temperature (Tg), amorphous vinylidene fluoride copolymer, blend of different types of polymers, polyethylene oxide and the like.

The gel electrolyte may be, for example, a mixture of a resin material, a solvent and a support salt. Examples of the resin material include polyacrylonitrile, copolymer of ethylene and acrylonitrile, and polymer obtained by crosslinking these materials. The solvent may be an organic solvent having a low molecular weight such as, for example, ethylene carbonate, propylene carbonate or the like. As the support salt, any of the materials described above is usable. The solid electrolyte and the gel electrolyte may also act as the separator 14.

An electricity storage device in this embodiment may be realized as any of various types of primary batteries, secondary batteries, capacitors other than the above-described lithium ion secondary battery. The capacitors may include an electrode including an electrode active material in the first embodiment and a counter electrode containing activated carbon.

EXAMPLES

Hereinafter, examples of the first and second embodiments will be described in detail. The present invention is not limited to the following examples.

1. Synthesis of Electrode Active Materials

1.1 Synthesis of 4,7-phenanthroline-5,6-dione (Compound (4))

4,7-phenanthroline-5,6-dione represented by formula (4) was synthesized by a method represented by the following reaction formula (III).

[Chemical formula 24]

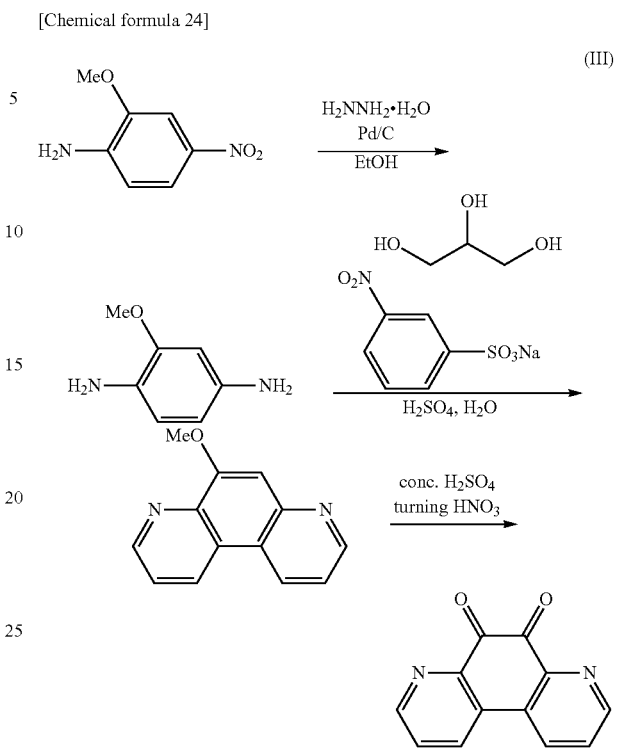

1.2 Synthesis of 1,4,5,8-tetraaza-9,10-anthraquinone (Compound (6))

1,4,5,8-tetraaza-9,10-anthraquinone represented by formula (6) was synthesized by a procedure represented by the following reaction formula (IV) in accordance with the description in documents (Liebigs Ann. Chem. 1963, 667, 55-58; J. Med. Chem. 1998, 41, 4716-4722)

[Chemical formula 25]

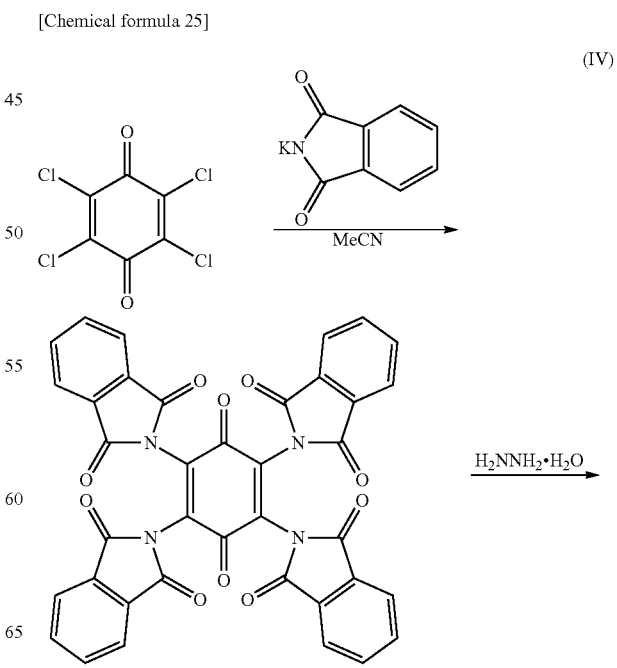

-continued

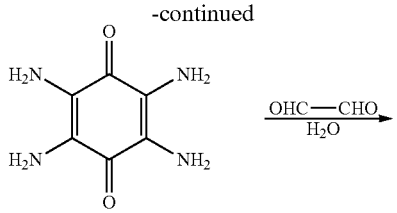

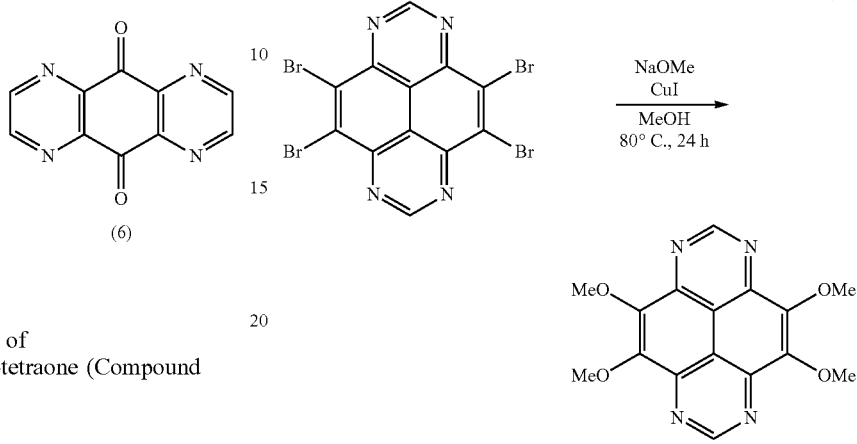

1.3 Synthesis of 1,3,6,8-tetraazapyrene-4,5,9,10-tetraone (Compound (5))

1,3,6,8-tetraazapyrene-4,5,9,10-tetraone represented by formula (5) was synthesized via a compound represented by formula (5a), a compound represented by formula (5b), a compound represented by formula (5c) and a compound represented by formula (5d). Hereinafter, synthesis of compound (5) will be described in an orderly fashion.

1,3,6,8-tetraazapyrene represented by formula (5a) was synthesized in accordance with a method described in a document (Chem. Heterocycl. Comp. 2011, 47, 916-917).

[Chemical formula 26]

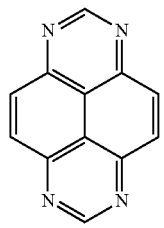

(5a)

1,3,6,8-tetraaza-4,5,9,10-tetrabromopyrene represented by formula (5b) was synthesized in accordance with a method described in a document (J. Org. Chem. 2012, 77, 6107-6116) by use of a compound represented by formula (5a) as a starting material.

[Chemical formula 27]

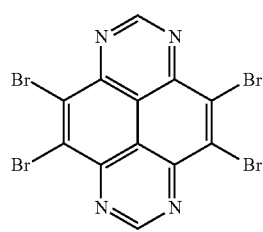

(5b)

1,3,6,8-tetraaza-4,5,9,10-tetramethoxypyrene represented by formula (5c) was synthesized by a method represented by the following reaction formula (IV).

[Chemical formula 28]

(IV)

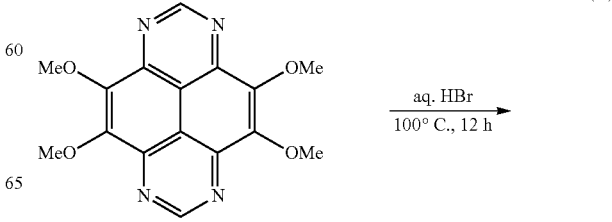

1,3,6,8-tetraaza-4,5,9,10-tetrabromopyrene (683 mg, 1.3 mmol), copper iodide (1.21 g, 6.4 mmol), sodium methoxide (927 mg, 17 mmol), and methanol (50 mL) were put into a round-bottom flask (100 ml), and the reaction solution was stirred at 80° C. for 24 hours under an argon atmosphere. After the temperature of the reaction solution was returned to room temperature, water (50 ml) was added to the reaction solution, and an organic substance was extracted by use of methylene chloride (50 ml, three times). The extracted organic substance was washed with an aqueous solution of ammonium chloride (20 ml, once), and then the solvent was removed by use of an evaporator. The resultant crude product was put to an alumina short column. As a result, 1,3,6,8-tetraaza-4,5,9,10-tetramethoxypyrene (290 mg, yield: 68%) was isolated as a yellow solid. This was subjected to $^1$H NMR analysis, $^{13}$C NMR analysis and mass spectrometry to obtain the following results.

$^1$H NMR (400 MHz, CDCl$_3$) δ 4.47 (s, 12H), 9.95 (s, 2H).

$^{13}$C NMR (100 MHz, CDCl$_3$) 663.1, 109.2, 150.0, 150.1, 156.9.

HRMS (APCI) m/z calcd for C$_{16}$H$_{15}$N$_4$O$_4$ [M+H]$^+$: 327.1088. found 327.1091.

1,3,6,8-tetraaza-4,5,9,10-tetrahydroxypyrene represented by formula (5d) was synthesized by a method represented by the following reaction formula (V).

[Chemical formula 29]

(V)

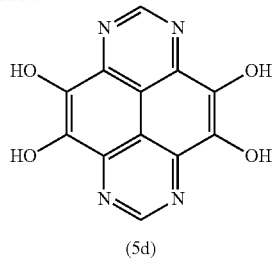

(5d)

1,3,6,8-tetraaza-4,5,9,10-tetramethoxypyrene (196 mg, 0.60 mmol) and 48% hydrobromic acid (20 mL) were put into a round-bottom flask (100 mL), and the reaction solution was stirred at 100° C. for 12 hours under an argon atmosphere. After the temperature of the reaction solution was returned to room temperature, water (50 mL) was added to the reaction solution, and the resultant solution was filtrated. The resultant solid was washed with water and dichloromethane and dried at low pressure. As a result, 1,3,6,8-tetraaza-4,5,9,10-tetrahydroxypyrene (151 mg, yield: 93%) was obtained as a black solid. This was subjected to $^1$H NMR analysis, $^{13}$C NMR analysis and mass spectrometry to obtain the following results.

$^1$H NMR (400 MHz, DMSO-d$_6$) δ 9.78 (s, 2H).
$^{13}$C NMR (100 MHz, DMSO-d$_6$) δ 102.9, 142.4, 145.5, 153.6.
HRMS (ESI) m/z calcd for $C_{12}H_5N_4O_4^-$ [M–H]$^-$: 269.0316. found 269.0313.

1,3,6,8-tetraazapyrene-4,5,9,10-tetraone represented by formula (5) was synthesized by a method represented by the following reaction formula (VI).

[Chemical formula 30]

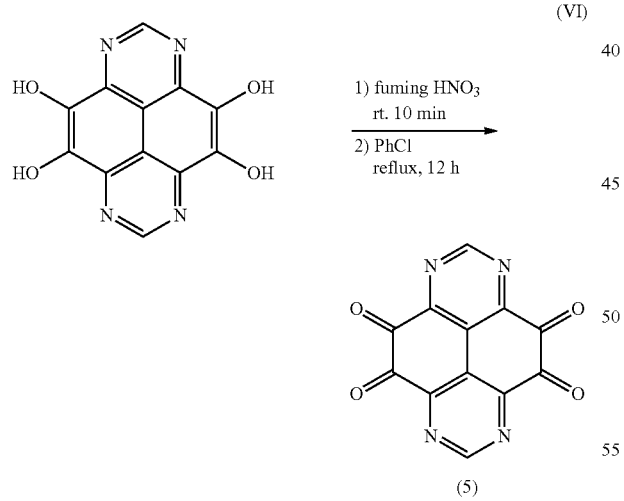

(VI)

1,3,6,8-tetraaza-4,5,9,10-tetrahydroxypyrene (124 mg, 0.46 mmol) and white fuming nitric acid (25 mL) were put into a round-bottom flask (100 mL), and the reaction solution was stirred at room temperature for 10 minutes. Water (50 mL) was added thereto, and then the resultant reaction solution was concentrated and washed with dichloromethane. As a result, a yellow solid was obtained. The obtained yellow solid and chlorobenzene (40 mL) were put into a round-bottom flask (100 mL), and the resultant solution was stirred for 12 hours while being refluxed. The temperature of the reaction solution was returned to room temperature, and the deposited precipitate was filtrated and then dried at low pressure. As a result, 1,3,6,8-tetraazapyrene-4,5,9,10-tetraone (64 mg, yield: 53%) was obtained as an orange solid. This was subjected to $^1$H NMR analysis, $^{13}$C NMR analysis and mass spectrometry to obtain the following results.

$^1$H NMR (400 MHz, DMSO-d$_6$) 69.63 (s, 2H).
$^{13}$C NMR (100 MHz, DMSO-d$_6$) 6123.4, 155.3, 159.4, 174.2.
HRMS (APCI) m/z calcd for $C_{12}H_2N_4O_4Cl_1$ [M+Cl]$^-$: 300.9759. found 300.9769.

1.4 Synthesis of poly[5,6-dioxo-4-(4-vinylbenzyl)-5,6-dihydro-4,7-phenanthroline-4-ium chloride] (Compound (15))

Poly[5,6-dioxo-4-(4-vinylbenzyl)-5,6-dihydro-4,7-phenanthroline-4-ium chloride] represented by formula (15) was synthesized by a method represented by the following reaction formula (VII).

[Chemical formula 31]

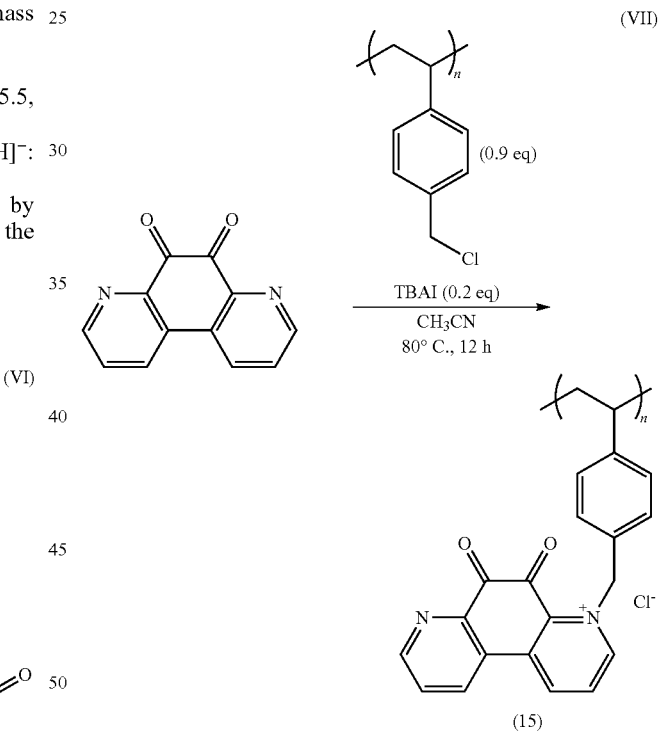

4,7-phenanthroline-5,6-dione (153 mg, 0.73 mmol), a 60/40 mixture of 3-isomer and 4-isomer of poly[vinylbenzyl chloride] (103 mg, average Mn: ≈55,000, average Mw: ≈100,000 by GPC/MALLS produced by Aldrich), tetrabutylammoniumiodide (64 mg, 0.17 mmol), and acetonitrile (5 mL) were put into a Schlenk flask (100 mL), and the reaction solution was stirred at 80° C. for 12 hours under an argon atmosphere. The temperature of the reaction solution was returned to room temperature, and the solution was filtrated. The resultant solid was washed with dichloromethane and methanol, and dried at low pressure. As a result, poly[5,6-dioxo-4-(4-vinylbenzyl)-5,6-dihydro-4,7-phenanthroline-4-ium chloride] (181 mg, yield: 47%) was obtained as a gray solid.

1.5 Synthesis of 2,9-dichloro-1,10-phenanthroline-5,6-dione (Compound (13))

2,9-dichloro-1,10-phenanthroline-5,6-dione represented by formula (13) was synthesized by a method represented by the following reaction formula (VIII).

2,9-dichloro-1,10-phenanthroline (1 g, 40.1 mmol) and KBr (4.76 g, 40.1 mmol, 10 eq.) were put into a 100 mL reactor, and were cooled in a dry ice-acetone bath to about −30° C. Concentrated sulfuric acid (20 mL) was slowly dripped thereto over about 10 minutes. After the dripping, the resultant suspension was stirred at the same temperature for 30 minutes, and then concentrated nitric acid (60%) (10 mL) was dripped thereto over about 3 minutes and stirred at the same temperature for 10 minutes. Then, the cooling bath was removed, and the temperature of the resultant solution was returned to room temperature. The resultant red suspension was stirred at room temperature for 1 hour, and then stirred while being heated at a bath temperature of 90° C. for 2 hours. After the heat was released, the resultant red solution was added to iced water (300 g), and the deposited crystals were filtrated. The substance extracted by the filtration was fully washed with tap water and air-dried. As a result, red powder (1.06 g) was obtained. The crystals were dissolved in acetone, and purified in a column by use of, first only chloroform, and then chloroform/acetone=4/1. As a result, pale orange powder (0.56 g, 2.01 mmol, 50%) was obtained.

[Chemical formula 32]

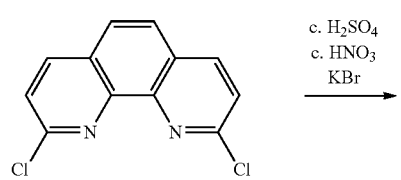

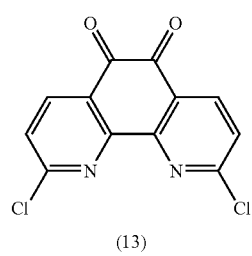

(VIII)

1.6 Synthesis of quinoxaline-5,8-dione (Compound (12))

Quinoxaline-5,8-dione represented by formula (12) was synthesized by a procedure represented by the following reaction formula (IX) in accordance with the description in a document (Australian Journal of Chemistry, 2010, 63, 1116-1121).

[Chemical formula 33]

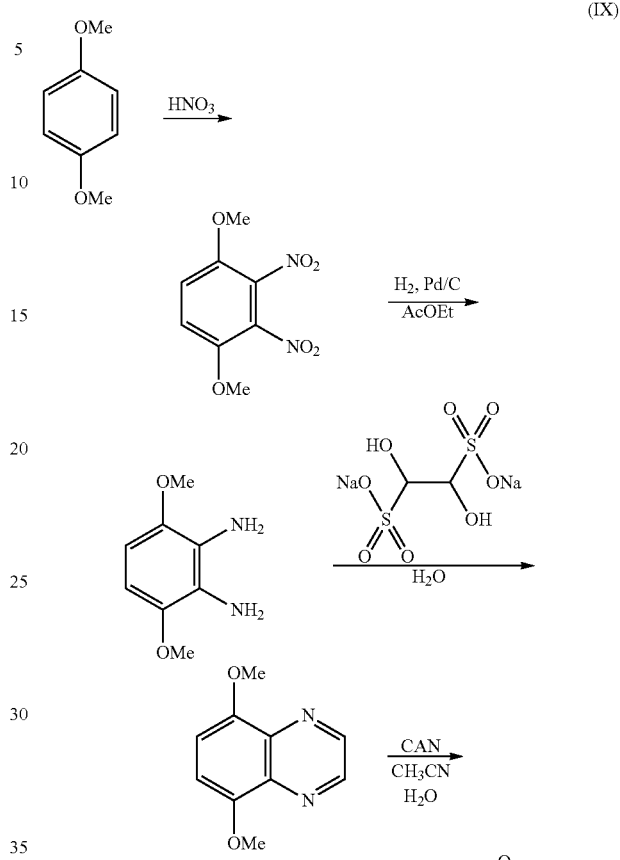

(IX)

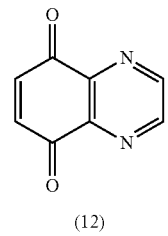

(12)

1.7 Synthesis of 1-methyl-5,8-dioxo-5,8-dihydroquinoxalinium trifluoromethanesulfonate (Compound (14))

1-methyl-5,8-dioxo-5,8-dihydroquinoxalinium trifluoromethanesulfonate represented by formula (14) was synthesized by a method represented by the following reaction formula (X).

[Chemical formula 34]

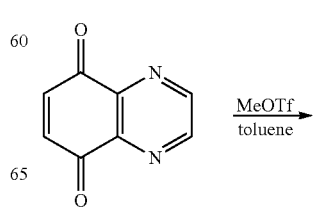

(X)

-continued

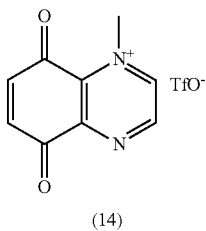

(14)

Quinoxaline-5,8-dione (49.6 mg, 0.310 mmol), methyl trifluoromethanesulfonate (108.3 mg, 0.660 mmol), and toluene (28 mL) were put into a round-bottom flask (100 ml), and the reaction solution was stirred at 75° C. for 12 hours under an argon atmosphere. After the temperature of the reaction solution was returned to room temperature, the deposited solid was washed with benzene (20 ml). As a result, 1-methyl-5,8-dioxo-5,8-dihydroquinoxaline-1-ium trifluoromethanesulfonate (61.1 mg, yield: 61%) was isolated as a reddish brown solid. This was subjected to $^1$H NMR analysis, $^{13}$C NMR analysis and mass spectrometry to obtain the following results.

$^1$H NMR (400 MHz, CD$_3$CN) δ 4.69 (s, 3H), 7.35 (d, J=10.6 Hz, 1H), 7.41 (d, J=10.6 Hz, 1H), 9.06 (d, J=3.2 Hz, 1H), 9.76 (d, J=3.2 Hz, 1H).

$^{13}$C NMR (100 MHz, CD$_3$CN) δ 51.3, 121.7 (q, J=318 Hz), 134.7, 139.0, 140.4, 145.4, 148.4, 155.1, 179.39, 179.45.

HRMS (ESI positive) m/z calcd for C$_9$H$_7$N$_2$O$_2^+$: 175.0502. found 175.0501.

HRMS (ESI negative) m/z calcd for CF$_3$O$_3$S$^-$: 148.9526. found 148.9524.

2. Assembly of Lithium Secondary Batteries

Example 1

A lithium ion secondary battery was produced by use of compound (4). First, compound (4) was pulverized in a mortar. The post-pulverization compound X had an average particle diameter of about 10 μm. 25 g of the pulverized compound X and 60 mg of acetylene black (conductor) were uniformly mixed, and 15 mg of polytetrafluoroethylene (binder) was added thereto and mixed. Thus, a positive electrode mix was prepared.

The positive electrode mix was applied to a positive electrode current collector formed of a metal wire net. The applied positive electrode mix was pressurized so as to be in pressure contact with the positive electrode current collector. Then, the resultant assembly was vacuum-dried to form a positive electrode active material layer on the positive electrode current collector. The positive electrode current collector and the positive electrode active material layer were punched to produce a discus-shaped positive electrode having a diameter of 13.5 mm. The amount of the applied positive electrode active material was 3.1 mg/cm$^2$ per unit surface area of the positive electrode.

A lithium ion secondary battery 10 having a structure described above with reference to FIG. 1 was produced using the produced positive electrode. First, a case 11 and a sealing plate 15 described above with reference to FIG. 1 were prepared. A positive electrode 21 was located in the case 11 such that the positive electrode current collector 12 would be in contact with an inner surface of the case 11. A separator 14 formed of a porous polyethylene sheet was located on the positive electrode 21. Next, an electrolyte 19 was put into the case. As the electrolyte 19, a non-aqueous solution obtained by dissolving lithium hexafluorophosphate in propylene carbonate at a concentration of 1 mol/liter was used. On an inner surface of the sealing plate 15, a 100 μm-thick discus-shaped lithium metal plate acting as a negative electrode current collector 17 and a negative electrode active material layer 16 was located. A gasket 18 was attached to the sealing plate 15. Then, the sealing plate 15 was put on the case 11, and the sealing plate 15 and the case 11 were caulked together by a pressing machine. As a result, a coin-shaped battery in example 1 was obtained. The battery was produced in a glovebox having an argon atmosphere and accommodating a gas purification device.

Example 2

A coin-shaped battery in example 2 was produced by substantially the same method as that in example 1 except that 1,10-phenanthroline-5,6-dione represented by formula (4') (produced by Tokyo Chemical Industry Co., Ltd.; hereinafter, referred to as "compound Y") was used as the positive electrode active material.

Example 3

A coin-shaped battery in example 3 was produced by substantially the same method as that in example 1 except that 1,4,5,8-tetraaza-9,10-anthraquinone represented by formula (6) was used as the positive electrode active material.

Example 4

A coin-shaped battery in example 4 was produced by substantially the same method as that in example 1 except that 1,3,6,8-tetraazapyrene-4,5,9,10-tetraone represented by formula (5) was used as the positive electrode active material.

Example 5

A coin-shaped battery in example 5 was produced by substantially the same method as that in example 1 except that poly[5,6-dioxo-4-(4-vinylbenzyl)-5,6-dihydro-4,7-phenanthroline-4-ium chloride] represented by formula (15) was used as the positive electrode active material.

Example 6

A coin-shaped battery in example 6 was produced by substantially the same method as that in example 1 except that 2,9-dichloro-1,10-phenanthroline-5,6-dione represented by formula (13) was used as the positive electrode active material.

Example 7

A coin-shaped battery in example 7 was produced by substantially the same method as that in example 1 except that quinoxaline-5,8-dione represented by formula (12) was used as the positive electrode active material.

Example 8

A coin-shaped battery in example 8 was produced by substantially the same method as that in example 1 except that 1-methyl-5,8-dioxo-5,8-dihydroquinoxalinium trifluoromethanesulfonate represented by formula (14) was used as the positive electrode active material.

Comparative Example 1

A coin-shaped battery in comparative example 1 was produced by substantially the same method as that in example 1 except that 9,10-phenanthrenequinone represented by the following (7) (produced by Tokyo Chemical Industry Co., Ltd.) was used as the positive electrode active material.

[Chemical formula 35]

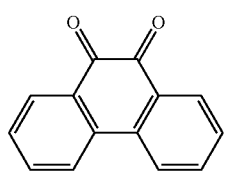

(7)

Comparative Example 2

A coin-shaped battery in comparative example 2 was produced by substantially the same method as that in example 1 except that anthraquinone (anthracene-9,10-dione) represented by the following formula (8) (produced by Tokyo Chemical Industry Co., Ltd.) was used as the positive electrode active material.

[Chemical formula 36]

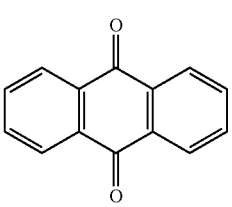

(8)

Comparative Example 3

A coin-shaped battery in example 5 was produced by substantially the same method as that in example 1 except that pyrene-4,5,9,10-tetraone represented by formula (9) was used as the positive electrode active material.

Pyrene-4,5,9,10-tetraone represented by formula (9) was synthesized in accordance with a method described in a document (J. Am. Chem. Soc. 2012, 134, 19694).

[Chemical formula 37]

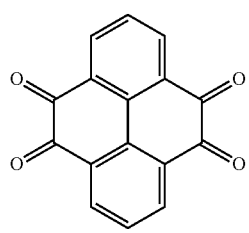

(9)

Comparative Example 4

A coin-shaped battery in comparative example 4 was produced by substantially the same method as that in example 1 except that 1,4-naphthoquinone represented by formula (10) was used as the positive electrode active material.

As 1,4-naphthoquinone represented by formula (10), a commercially available product (produced by Tokyo Chemical Industry Co., Ltd.) was used

[Chemical formula 38]

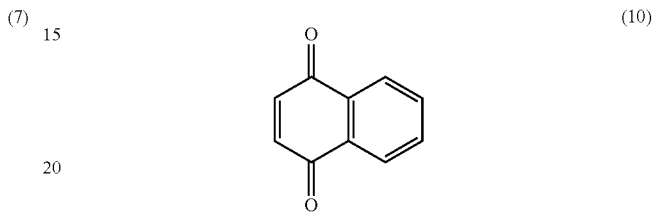

(10)

2. Results of Charge/Discharge Test and Consideration Thereon

Figure 2:
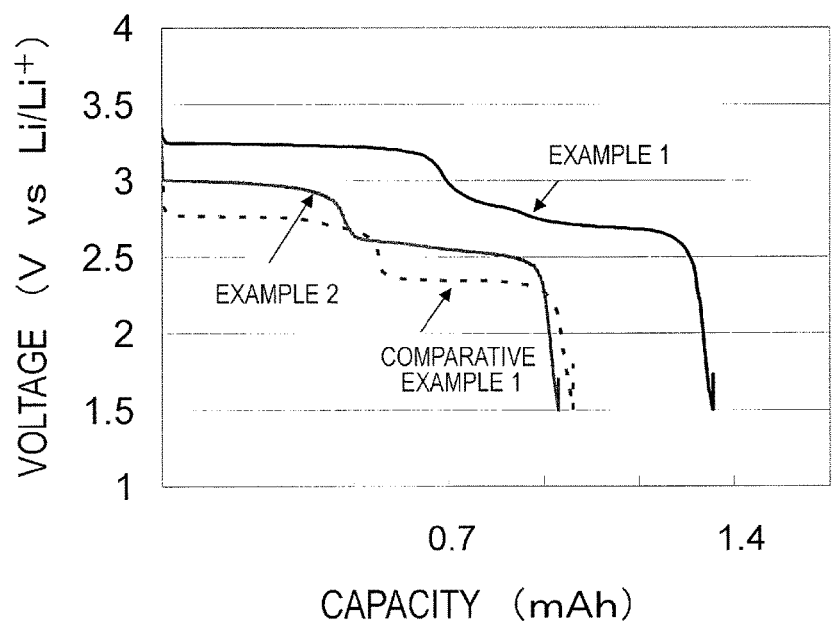
FIG. 2 shows charge/discharge curves of batteries in example 1, example 2 and comparative example 1.
Figure 3:
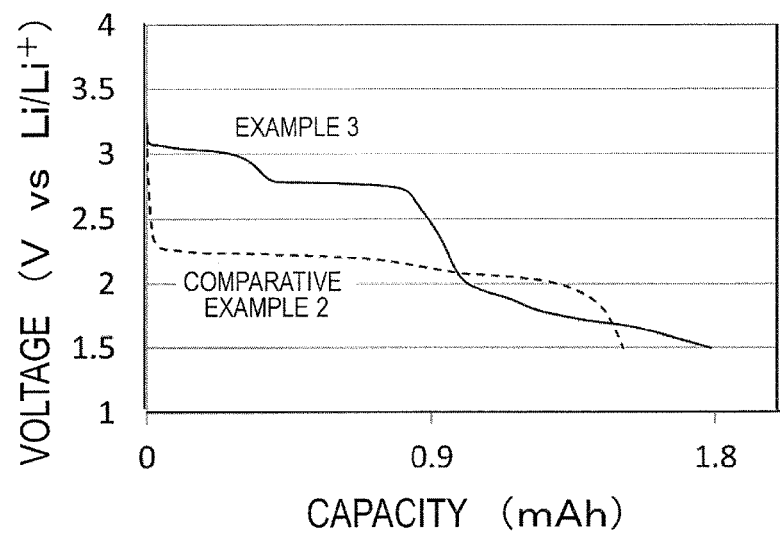
FIG. 3 shows charge/discharge curves of batteries in example 3 and comparative example 2.
Figure 4:
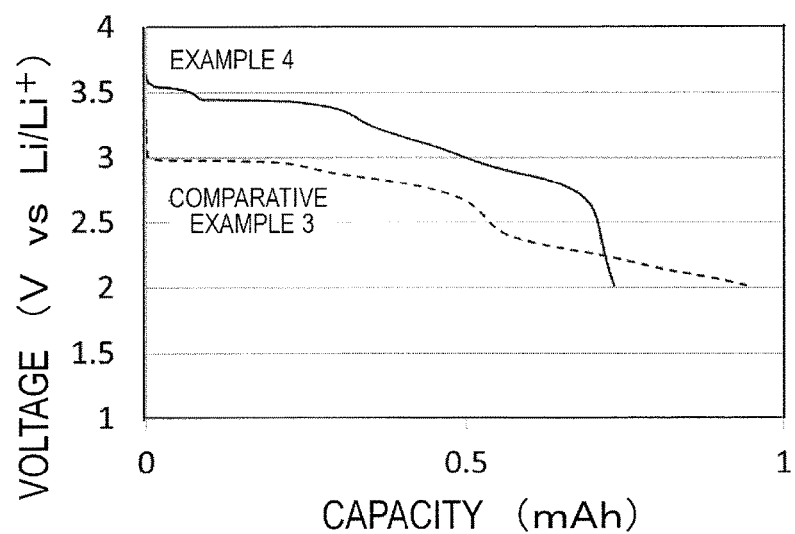
FIG. 4 shows charge/discharge curves of batteries in example 4 and comparative example 3.
Figure 5:
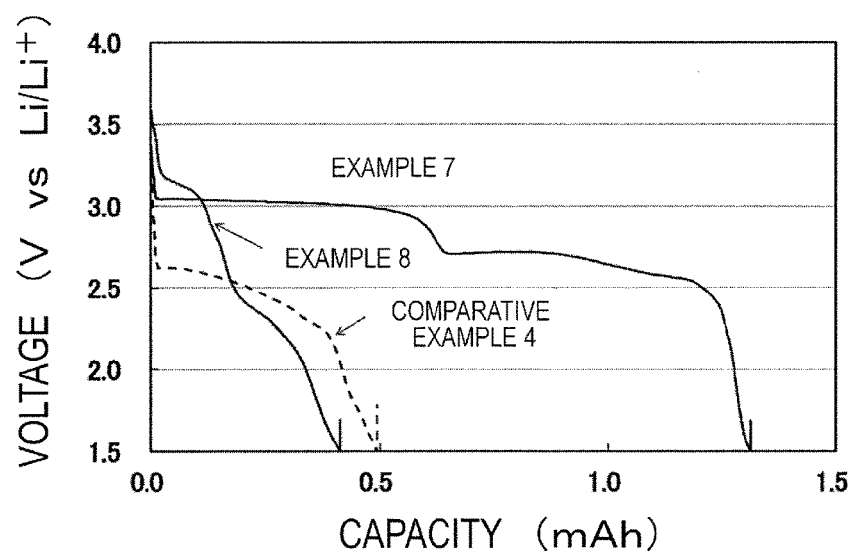
FIG. 5 shows charge/discharge curves of batteries in example 7, example 8 and comparative example 4.

A charge/discharge test was performed on the batteries in examples 1 through 8 and comparative examples 1 through 4 as follows. As the current value, a value of 0.2 C rate (5 hour rate) with respect to the theoretical capacity of each battery was used. For the batteries in example 4 and comparative example 3, the voltage range was 2.0 to 4.0 V. For the other batteries, the voltage range was 1.5 to 4.0 V. The charge/discharge test was started with discharge. Between discharge and charge, and between charge and discharge, a pause time of 5 minutes was provided. The discharge potential at the third cycle was measured. The results are shown in Tables 1 through 4 together with the theoretical capacity per unit weight of each active material. FIG. 2 shows charge/discharge curves of the batteries in example 1, example 2 and comparative example 1. FIG. 3 shows charge/discharge curves of the batteries in example 3 and comparative example 2. FIG. 4 shows charge/discharge curves of the batteries in example 4 and comparative example 3. FIG. 5 shows charge/discharge curves of the batteries in example 7, example 8 and comparative example 4.

TABLE 1

| | Compound | Theoretical capacity [mAh/g] | 1st discharge potential [V vs Li/Li] | 2nd discharge potential [V vs Li/Li] |
| --- | --- | --- | --- | --- |
| Example 1 | (4) | 255 | 3.25 V | 2.69 V |
| Example 2 | (4') | 255 | 3.01 V | 2.53 V |
| Example 5 | (15) | 163 | 3.12 V | 2.68 V |
| Example 6 | (13) | 192 | 3.10 V | 2.65 V |
| Comparative example 1 | (7) | 257 | 2.78 V | 2.33 V |

TABLE 2

| | Compound | Theoretical capacity [mAh/g] | 1st discharge potential [V vs Li/Li] | 2nd discharge potential [V vs Li/Li] |
| --- | --- | --- | --- | --- |
| Example 3 | (6) | 253 | 2.9 V (3.03 and 2.77 V) | 1.75 V |

TABLE 2-continued

| | Compound | Theoretical capacity [mAh/g] | 1st discharge potential [V vs Li/Li] | 2nd discharge potential [V vs Li/Li] |
|---|---|---|---|---|
| Comparative example 2 | (8) | 257 | 2.22 V | 2.01 V |

TABLE 3

| | Compound | Theoretical capacity [mAh/g] | 1st discharge potential [V vs Li/Li] | 2nd discharge potential [V vs Li/Li] |
|---|---|---|---|---|
| Example 4 | (5) | 403 | 3.54, 3.43 V | 2.99 V |
| Comparative example 3 | (9) | 409 | 2.97 V | 2.35 V |

TABLE 4

| | Compound | Theoretical capacity [mAh/g] | 1st discharge potential [V vs Li/Li] | 2nd discharge potential [V vs Li/Li] |
|---|---|---|---|---|
| Example 7 | (12) | 335 | 3.03 V | 2.67 V |
| Example 8 | (14) | 165 | 3.14 V | 2.31 V |
| Comparative example 4 | (10) | 339 | 2.52 V | 2.35 V |

As shown in Tables 1 through 4, the batteries in examples 1 through 8 and comparative examples 1 through 4 all showed a discharge behavior having two-stage flat areas. A discharge voltage showing the first-stage reduction reaction (corresponding to the reaction on the left side of formulas (I) and (II)) was observed at around 3.2 V in example 1, at around 3 V in example 2, at around 3.1 V in example 5, and at around 2.8 V in comparative example 1. A discharge voltage showing the second-stage reduction reaction (corresponding to the reaction on the right side of formulas (I) and (II)) was observed at around 2.7 V in example 1, at around 2.5 V in example 2, at around 2.7 V in example 5, and at around 2.3 V in comparative example 1.

The discharge voltage in example 2 was higher by 0.2 V than that in comparative example 1 (9,10-phenanthrenequinone), but the discharge flat area on the high voltage side in example 1 was higher by about 0.5 V than that in comparative example 1. The tetraketone compounds used in examples 1 and 2 do not have substituents. Therefore, the rise in the discharge voltage is considered to be an effect derived from the framework, not from introduction of substituents or the like.

As can be understood from the results in example 2 and comparative example 1, introduction of merely nitrogen atoms into the framework of 9,10-phenanthrenequinone provides an effect of raising the discharge voltage of the battery by about 0.2 V. By contrast, in the compound used in example 1, an oxygen atom and a nitrogen atom of each carbonyl group are present on the aromatic ring while having two carbon atoms therebetween. The nitrogen atom changes the bond (coordination structure) of lithium and the heteroaromatic ring in a discharge state. Therefore, the compound in example 1 is considered to realize discharge at a higher potential than the compound in example 2.

As can be seen from a comparison of examples 1 and 2 against comparative example 1, the voltage was raised although the theoretical capacities of the batteries as reaction frameworks were almost the same.

In example 6, the discharge voltage was 3.10 V on the first stage and 2.65 V on the second stage. The voltages were higher by about 0.4 V than those in comparative example 1. The compound in example 6 was obtained merely by substituting a part of the hydrogen atoms of the compound in example 2 with chlorine atoms. Nonetheless, the voltages in example 6 were higher by about 0.1 V than those in example 2. From this, it is considered that introduction of nitrogen atoms into an aromatic ring provides an effect of raising the reduction potential (battery voltage) regardless of the type of the substituent in the heteroaromatic ring. It has also been confirmed that introduction of electron-withdrawing substituents such as halogen atoms or the like into a heteroaromatic ring further raises the reduction potential.

It has been confirmed from a comparison between example 5 and example 1 that when a nitrogen atom is contained in a heteroaromatic ring, an effect of raising the discharge voltage is provided even through the heteroaromatic ring has a polymer structure.

A discharge voltage showing the first-stage reduction reaction (corresponding to the reaction on the left side of formulas (I) and (II)) was observed at around 2.9 V in example 3 (in more detail, observed at two stages of 3.03 V and 2.77 V) and at around 2.2 V in comparative example 2. A discharge voltage showing the second-stage reduction reaction (corresponding to the reaction on the right side of formulas (I) and (II)) was observed at around 1.8 V in example 3 and at around 2.0 V in comparative example 2. Where the average of the first-stage voltage and the second-stage voltage is the average voltage, the average voltage was 2.35 V in example 3 and 2.1 V in comparative example 2. As can be seen from these results, introduction of nitrogen atoms into the framework of anthraquinone is considered to provide an effect of raising the discharge voltage of the battery by about 0.2 to 0.3 V.

It has been confirmed from a comparison between example 3 and comparative example 2 that the discharge voltage can be raised although the theoretical capacities per unit weight as reaction frameworks involved in redox are almost the same.

A discharge voltage showing the first-stage reduction reaction (corresponding to the reaction on the left side of formulas (I) and (II)) was observed at around 3.03 V in example 7 and at around 2.52 V in comparative example 4. A discharge voltage showing the second-stage reduction reaction (corresponding to the reaction on the right side of formulas (I) and (II)) was observed at around 2.67 V in example 7 and at around 2.36 V in comparative example 4. As can be seen from these results, introduction of nitrogen atoms into the framework of naphthoquinone is considered to provide an effect of raising the discharge voltage of the battery by about 0.3 to 0.5 V.

It has been confirmed from a comparison between example 7 and comparative example 4 that the discharge voltage can be raised although the theoretical capacities per unit weight as reaction frameworks involved in redox are almost the same.

A discharge voltage showing the first-stage reduction reaction (corresponding to the reaction on the left side of formulas (I) and (II)) was observed at around 3.14 V in example 8 and at around 2.52 V in comparative example 4. A discharge voltage showing the second-stage reduction reaction (corresponding to the reaction on the right side of formulas (I) and (II)) was observed at around 2.31 V in example 8 and at around 2.36 V in comparative example 4.

As can be seen from these results, introduction of nitrogen atoms into the framework of naphthoquinone and also of alkyl groups into the nitrogen atoms in the framework is considered to provide an effect of raising the discharge voltage of the battery by about 0.6 V in the case where the framework of naphthoquinone is of quaternary ammonium ion.

A discharge voltage showing the first-stage reduction reaction (corresponding to the reaction on the left side of formulas (I) and (II)) was observed at around 3.5 V in example 4 (in more detail, observed at two stages of 3.54 V and 3.43 V) and at around 3.0 V in comparative example 3. A discharge voltage showing the second-stage reduction reaction (corresponding to the reaction on the right side of formulas (I) and (II)) was observed at around 3.0 V in example 4 and at around 2.3 V in comparative example 3. As can be seen from these results, introduction of nitrogen atoms into the framework of pyrenetetraone is considered to provide an effect of raising the discharge voltage of the battery by about 0.5 to 0.7 V.

From these results, it has been shown that a heteroaromatic compound represented by general formula (2) in which four ketone groups are introduced into symmetrical positions of a pyrene ring is effective to realize an electricity storage device having a high discharge voltage. A conceivable reason for this is as follows. Like in the compound used in example 1 (4,7-phenanthroline-5,6-dione represented by formula (4)), an oxygen atom and a nitrogen atom of each carbonyl group are present on the aromatic ring while having two carbon atoms therebetween. The nitrogen atom changes the bond (coordination structure) of lithium and the heteroaromatic ring in a discharge state. This is why the compound in example 4 is considered to realize discharge at a still higher potential. As can be seen from a comparison between examples 4 and comparative example 3, the voltage was raised although the theoretical capacities of the batteries as reaction frameworks were almost the same.

As can be understood from the results in example 2 and comparative example 1 and the results in example 4 and comparative example 3, introduction of nitrogen atoms into the framework of 9,10-phenanthrenequinone provides an effect of raising the discharge voltage of the battery by about 0.2 V. By contrast, in the compound (4) used in example 1, an oxygen atom and a nitrogen atom of each carbonyl group are present on the aromatic ring while having two carbon atoms therebetween. The nitrogen atom changes the bond (coordination structure) of lithium and the heteroaromatic ring in a discharge state. Therefore, the compound in example 1 is considered to realize discharge at a higher potential than the compound in example 2.

Namely, the following has been found: introduction of nitrogen atoms into an aromatic ring including carbonyl groups can raise the redox potential; and appropriate selection of the introduction position of the nitrogen atom, specifically, locating an oxygen atom and a nitrogen atom of each carbonyl group at positions, on the aromatic ring, which have two carbon atoms therebetween, can realize an electrode active material that can be discharged at a higher voltage. From the results in example 3 and comparative example 2, it is considered that substantially the same effect is provided by an aromatic ring having any other framework although the degree of the effect of raising the discharge voltage depends on the framework of the aromatic ring.

The battery in example 5 and the battery in comparative example 1 were charged/discharged 20 times in repetition. The discharge capacity maintenance ratio with respect to the initial discharge capacity was 98% in example 5 and 25% in comparative example 1. After the cycle test, the batteries were decomposed and the coloring behavior of the electrolytic solution in each battery was observed. In the battery in comparative example 1, the electrolytic solution was colored green. This suggests that the electrode active material was dissolved in the electrolytic solution. By contrast, in the battery in example 5, the electrolytic solution was not colored. This suggests that the amount of the electrode active material that was dissolved in the electrolytic solution was extremely small. These result show the following: introduction of nitrogen atoms into an aromatic ring including carbonyl groups raises the redox potential, and the properties of the resultant substance are not changed even when the substance is polymerized; and in addition, solubility of the electrode active material in the electrolytic solution is significantly suppressed, and therefore a battery having excellent cycle characteristics is obtained. The compound (15) in example 15 is obtained by substituting the nitrogen atom included in the heteroaromatic ring of the compound (4) in example 1 with a substituent, and is a polymer bonded to a main chain via the substituents. It is easily estimated analogically that the other compounds used in example 2, example 3, example 4 and the like can each be used in substantially the same manner to produce an electrode active material formed of a polymer that has excellent cycle characteristics.

INDUSTRIAL APPLICABILITY

An electrode active material according to the present invention is suitable for an electricity storage device, especially an electricity storage device using a non-aqueous electrolyte. An electricity storage device according to the present invention is preferably usable for power sources of mobile electronic devices, power sources of transportation devices, uninterruptible power supplies, and the like.

REFERENCE SIGNS LIST

11 Case
12 Positive electrode current collector
13 Positive electrode active material layer
14 Separator
15 Sealing plate
16 Negative electrode active material layer
17 Negative electrode current collector
18 Gasket
19 Electrolyte
21 Positive electrode
22 Negative electrode

The invention claimed is:
1. An electrode comprising a heteroaromatic compound including two or more carbonyl groups and containing two or more nitrogen atoms,
   wherein carbon atoms of the two or more carbonyl groups and the two or more nitrogen atoms are included in a framework of the heteroaromatic compound, and
   wherein the electrode is configured to repeatedly charge and discharge,
   and wherein:
   the heteroaromatic compound is represented by the following general formula (1), (2) or (3), and
   in the general formulas (1), (2) and (3), $R_1$ through $R_6$, $R_{10}$, $R_{11}$, and $R_{21}$ through $R_{24}$ are independently a hydrogen atom, a halogen atom, a phenyl group which may include a substituent, a complex ring group which may include a substituent, or a hydrocarbon group of a carbon number of 1 through 4 which may include a substituent:

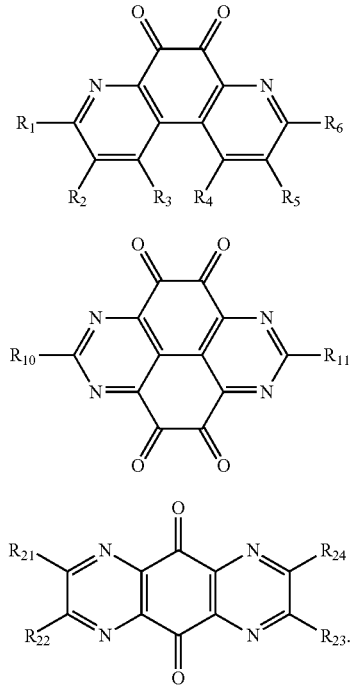

(1)

(2)

(3)

2. The electrode of claim 1, wherein the heteroaromatic compound is represented by the following chemical formula (4) or (6)

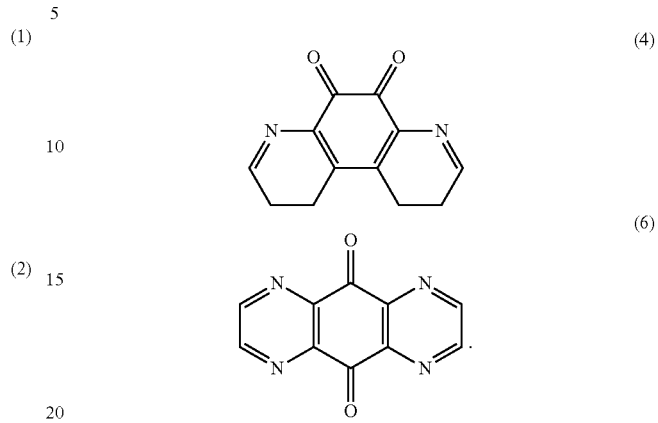

(4)

(6)

3. An electricity storage device, comprising:
  a positive electrode, a negative electrode, and an electrolyte;
  wherein at least one selected from the positive electrode and the negative electrode includes an electrode active material for an electricity storage device of claim 1 as an electrode active material.

4. The electricity storage device of claim 3, wherein the electrode is configured to repeatedly charge and discharge.

* * * * *